United States Patent
Perrin et al.

(10) Patent No.: US 10,980,600 B2
(45) Date of Patent: Apr. 20, 2021

(54) METHOD OF ASSISTING THE PRODUCTION OF AN IMPLANTABLE UNFURLABLE MADE TO MEASURE DEVICE

(71) Applicants: INSTITUT MINES-TÉLÉCOM, Paris (FR); UNIVERSITE JEAN MONNET SAINT ETIENNE, Saint-Etienne (FR); CENTRE HOSPITALIER UNIVERSITAIRE DE SAINT-ETIENNE, Saint-Etienne (FR)

(72) Inventors: David Perrin, Saint-Etienne (FR); Stéphane Avril, Saint-Etienne (FR); Pierre Badel, La Tour en Jarez (FR); Jean-Noël Albertini, Sorbiers (FR)

(73) Assignees: Institut Mines-Telecom, Paris (FR); Universite Jean Monnet Saint Etienne, Saint Etienne (FR); Centre Hospitalier Universitaire de Saint-Etienne, Saint Etienne (FR)

( * ) Notice: Subject to any disclaimer, the term of this patent is extended or adjusted under 35 U.S.C. 154(b) by 117 days.

(21) Appl. No.: 16/343,369

(22) PCT Filed: Sep. 18, 2017

(86) PCT No.: PCT/FR2017/052486
§ 371 (c)(1),
(2) Date: Apr. 18, 2019

(87) PCT Pub. No.: WO2018/073505
PCT Pub. Date: Apr. 26, 2018

(65) Prior Publication Data
US 2019/0239958 A1    Aug. 8, 2019

(30) Foreign Application Priority Data
Oct. 18, 2016   (FR) ...................................... 1660082

(51) Int. Cl.
*A61B 34/10* (2016.01)
*G06T 7/12* (2017.01)
(Continued)

(52) U.S. Cl.
CPC ................ *A61B 34/10* (2016.02); *A61F 2/07* (2013.01); *G06T 7/0012* (2013.01); *G06T 7/12* (2017.01);
(Continued)

(58) Field of Classification Search
CPC .......... A61B 2017/00526; A61B 2017/00778; A61B 34/10; A61B 2034/102;
(Continued)

(56) References Cited

U.S. PATENT DOCUMENTS

2015/0112659 A1* 4/2015 Mortier .................. G06T 17/20
703/11

FOREIGN PATENT DOCUMENTS

WO    2013171039 A1    11/2013
WO    2015089118 A1    6/2015
(Continued)

OTHER PUBLICATIONS

Auricchio et al. "Carotid artery stenting simulation: from patient-specific images to finite element analysis." Medical engineering & physics 33.3 (2011): 281-289. (Year: 2011).*
(Continued)

*Primary Examiner* — Katrina R Fujita

(57) ABSTRACT

The method of assisting the production of an implantable unfurlable made to measure device comprises: three-dimensional reconstruction of a complex surface of the cavity in which the device will be implanted; Production of a first finite element mesh of this complex surface; Choosing of generic components of the device; Production of a second finite element mesh of these assembled generic components;
(Continued)

Determination of the morphosis parameters for morphosing from the first mesh to a mesh of a set of simple linked volumes which is representative of the part of the cavity, and then deformation of the first mesh by this morphosis; Simulation of a deformation of the second mesh, by inverse morphosis dependent on the determined parameters, to the complex surface, simulating unfurling of the device; Determination of dimensioning of points of interest by projection onto the second deformed mesh; and Generation of a production blueprint plan of the device.

11 Claims, 3 Drawing Sheets

(51) Int. Cl.
*A61F 2/07* (2013.01)
*G06T 7/00* (2017.01)
*A61B 90/00* (2016.01)
*A61B 17/00* (2006.01)
*A61F 2/06* (2013.01)

(52) U.S. Cl.
CPC ............... *A61B 2017/00526* (2013.01); *A61B 2017/00778* (2013.01); *A61B 2034/102* (2016.02); *A61B 2034/105* (2016.02); *A61B 2034/108* (2016.02); *A61B 2090/367* (2016.02); *A61F 2/06* (2013.01); *A61F 2002/065* (2013.01); *A61F 2240/002* (2013.01)

(58) Field of Classification Search
CPC ........ A61B 2034/105; A61B 2034/108; A61B 2090/367; A61F 2/06; A61F 2/07; A61F 2002/065; A61F 2240/002; G06T 7/0012; G06T 7/12
See application file for complete search history.

(56) References Cited

FOREIGN PATENT DOCUMENTS

| WO | 2015101545 A1 | 7/2015 |
|---|---|---|
| WO | 2018073505 A1 | 4/2018 |

OTHER PUBLICATIONS

Auricchio et al. "Patient-specific aortic endografting simulation: From diagnosis to prediction." Computers in biology and medicine 43.4 (2013): 386-394. (Year: 2013).*

Foreign Communication from a Related Counterpart Application, International Search Report dated Nov. 9, 2017, International Application No. PCT/FR2017/052486 filed on Sep. 18, 2017.

Foreign Communication from a Related Counterpart Application, Written Opinion dated Nov. 9, 2017, International Application No. PCT/FR2017/052486 filed on Sep. 18, 2017.

* cited by examiner

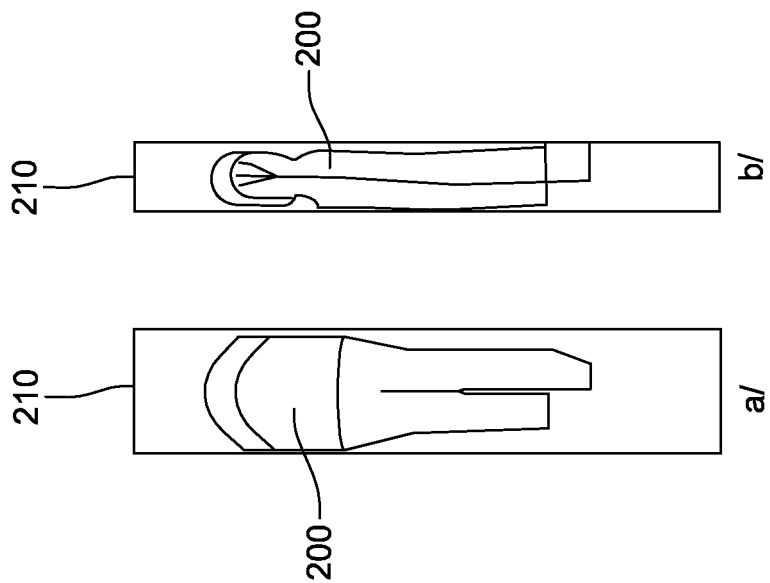
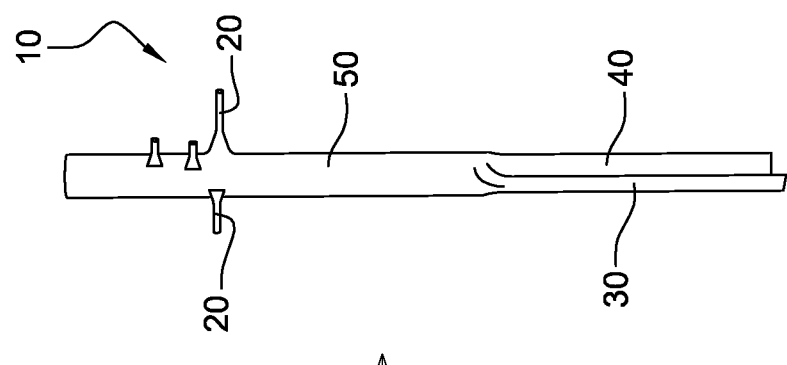
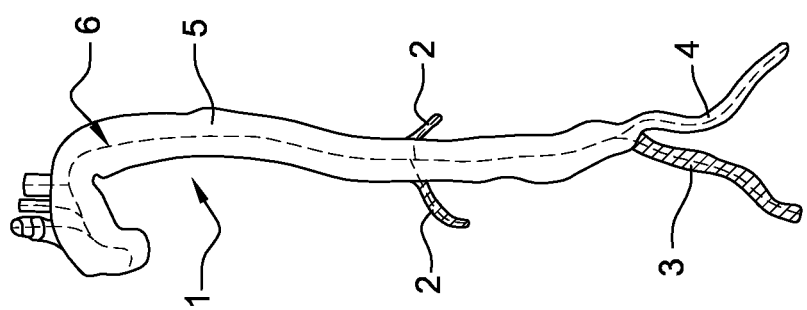

METHOD OF ASSISTING THE PRODUCTION OF AN IMPLANTABLE UNFURLABLE MADE TO MEASURE DEVICE

CROSS-REFERENCE TO RELATED APPLICATIONS

The present application is a filing under 35 U.S.C. 371 as the National Stage of International Application No. PCT/FR2017/052486, filed Sep. 18, 2017, entitled "METHOD OF ASSISTING THE PRODUCTION OF AN IMPLANTABLE UNFURLABLE MADE TO MEASURE DEVICE," which claims priority to French Application No. 1660082 filed with the Intellectual Property Office of France on Oct. 18, 2016, both of which are incorporated herein by reference in their entirety for all purposes.

The invention concerns a method for assisting in the production of an implantable unfurlable made-to-measure device that can be implanted in a cavity of a body of a living being. In particular, the method according to the invention is based on a series of radiographic images of the cavity.

At present, in order to produce a made-to-measure vascular endoprosthesis adapted to a given patient, simple geometric measurements of the target artery segment are taken from images from a preoperative scan of the patient. These measurements include the distance between the ostia of the collateral arteries opening in the target segment, the angulation of same, etc. However, the difficulty of taking three-dimensional measurements, and the difficulty of anticipating deformations in endoprostheses in the patient therefore require a huge amount of experience and time, both of the practitioner who is going to perform the implantation operation and of the clinical associates of endoprosthesis manufacturers tasked with producing the made-to-measure endoprosthesis. Moreover, as a result of uncertainties concerning the accuracy of the dimensioning of made-to-measure endoprostheses, some endoprosthesis manufacturers validate the measured dimensioning by means of an in vitro implantation of an endoprosthesis prototype in a model of the target artery segment of the patient obtained by three-dimensional printing. In practice, such in vitro validation requires several prototypes to be created. These endoprostheses are therefore subject to high additional costs, in comparison with generic prostheses, and a long delivery time that is prohibitive for patients who need to be operated on swiftly. Document US2013/0296998 describes an embodiment of a three-dimensional printed model of a target artery segment for producing a made-to-measure endoprosthesis.

One aim of the invention is to provide a method for assisting in the production of an implantable unfurlable made-to-measure device that can be implanted in a cavity of a body of a living being that is simple, quick and economical.

To this end, the invention concerns a method for assisting in the production of an implantable unfurlable made-to-measure device that can be implanted in a cavity of a body of a living being, based on a series of radiographic images of the cavity, the method comprising steps of:

a. Three-dimensional reconstruction of a complex surface delimiting a part of the cavity in which the unfurlable made-to-measure device is intended to be installed;
b. Production of a first finite element mesh of a geometry of the complex surface thus reconstructed;
c. Choosing of one or more generic components of the unfurlable made-to-measure device that is to be personalized;
d. Production of a second finite element mesh of the generic component or components chosen and assembled to form the unfurlable made-to-measure device;
e. Determination of the parameters of a morphing of the obtained first mesh to a mesh of a geometry formed from a set of simple volumes linked to each other representative of the part of the cavity, and then deformation of the first mesh by this morphing;
f. Simulation, by the finite elements method, of the deformation of the second mesh thus obtained, by inverse morphing dependent on the previously determined morphing parameters, to the geometry of the complex surface of the cavity, so as to simulate the unfurling of the unfurlable made-to-measure device once installed in the cavity;
g. Determination of a dimensioning of points of interest of the part in question of the cavity by projecting them onto the second mesh thus deformed; and
h. Generation of a dimensioned drawing of the generic component or components onto which the previously determined dimensioning has been transposed, the dimensioned drawing allowing the unfurlable made-to-measure device to be produced.

Therefore, the method for assisting in the production of an implantable unfurlable made-to-measure device that can be implanted in a cavity of a body of a living being according to the invention thus makes is possible to digitally dimension implantable devices such that they are personalized to the patient to be operated on, in the preoperative planning phase, before the surgical implantation operation on the patient, in a manner that is simple and quick, while also remaining economical.

Advantageously, but optionally, the method according to the invention comprises at least one of the following additional technical features:

during step b, the method comprises a sub-step of determining geometric parameters of points of interest of the part in question of the cavity, the geometric parameters being used during step g;

following step e and prior to step f, the second mesh undergoes a deformation simulating a compression of the assembled unfurlable made-to-measure device inside a delivery sheath;

during step f, the method comprises a preliminary step of inserting the second mesh into the deformed first mesh;

following step f and prior to step g, the method comprises a step of calculating, by simulation by the finite elements method, deformations and constraints induced by interactions between the first and second meshes following the deformation by inverse morphing of the second mesh to the first mesh;

during step g, the projection consists in determining the nodes of the second mesh facing the points of interest;

during step h, the transposing of the dimensioning is carried out based on the coordinates of the nodes previously determined during step g in the non-deformed second mesh;

following the deformation simulating a compression, the deformed second mesh undergoes a simulation of insertion into the first mesh into a position close to an optimal position;

the method comprises an additional step of
i—Extracting a set of indicators enabling a practitioner to determine the suitability of a preoperative plan;
the cavity being an arterial lumen, the unfurlable made-to-measure device is an aortic endoprosthesis.

Moreover, the invention also concerns a computer medium comprising the recording of a program for controlling a calculator, for implementing the method according to the invention having at least one of the preceding features.

Other features and advantages of the invention are disclosed in the description that follows of one embodiment of the method. In the appended drawings:

FIG. 1a is a three-dimensional view of a finite element mesh of a target artery segment;

FIG. 1b is a three-dimensional view of a morphing of the target artery segment of FIG. 1a by the method according to the invention;

FIG. 2a is a front view of a finite element mesh of a made-to-measure endoprosthesis during preparation;

FIG. 2b is a front view of the mesh of FIG. 2a in a compressed configuration inside a delivery sheath;

Figure 4:
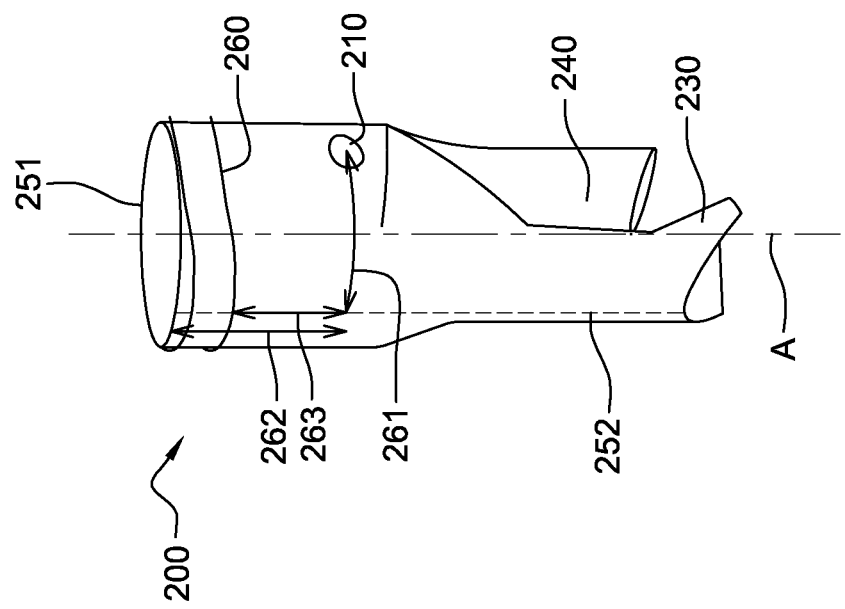
FIG. 4 is a schematic view showing the dimensioning of the made-to-measure endoprosthesis and the positioning of the fenestra on the mesh of the endoprosthesis of FIG. 2a, by the method according to the invention; and, FIG. 5 is a logical diagram of the method according to the invention.
Figure 3:
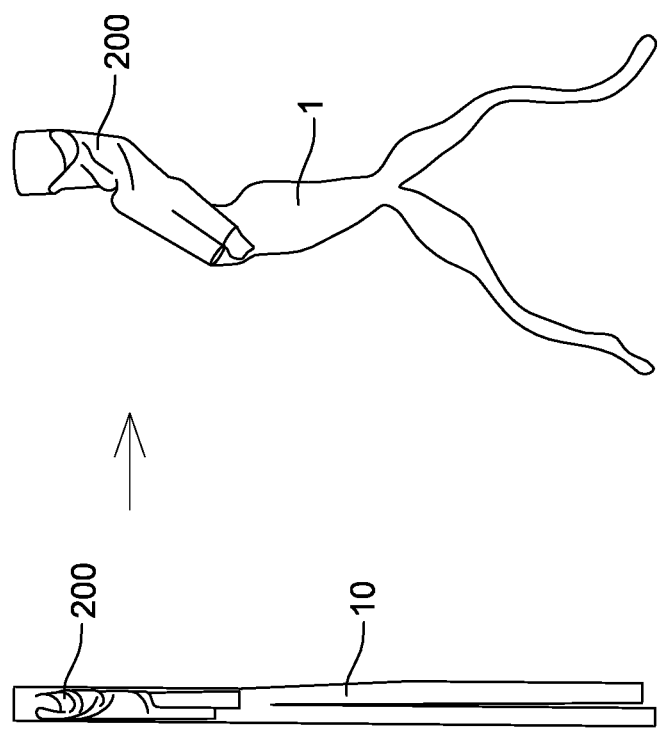
FIG. 3 is a view showing the morphing of the mesh of FIG. 2b implanted in the morphed target artery segment of FIG. 1b to the target artery segment of FIG. 1a, by the method according to the invention.
Figure 5:
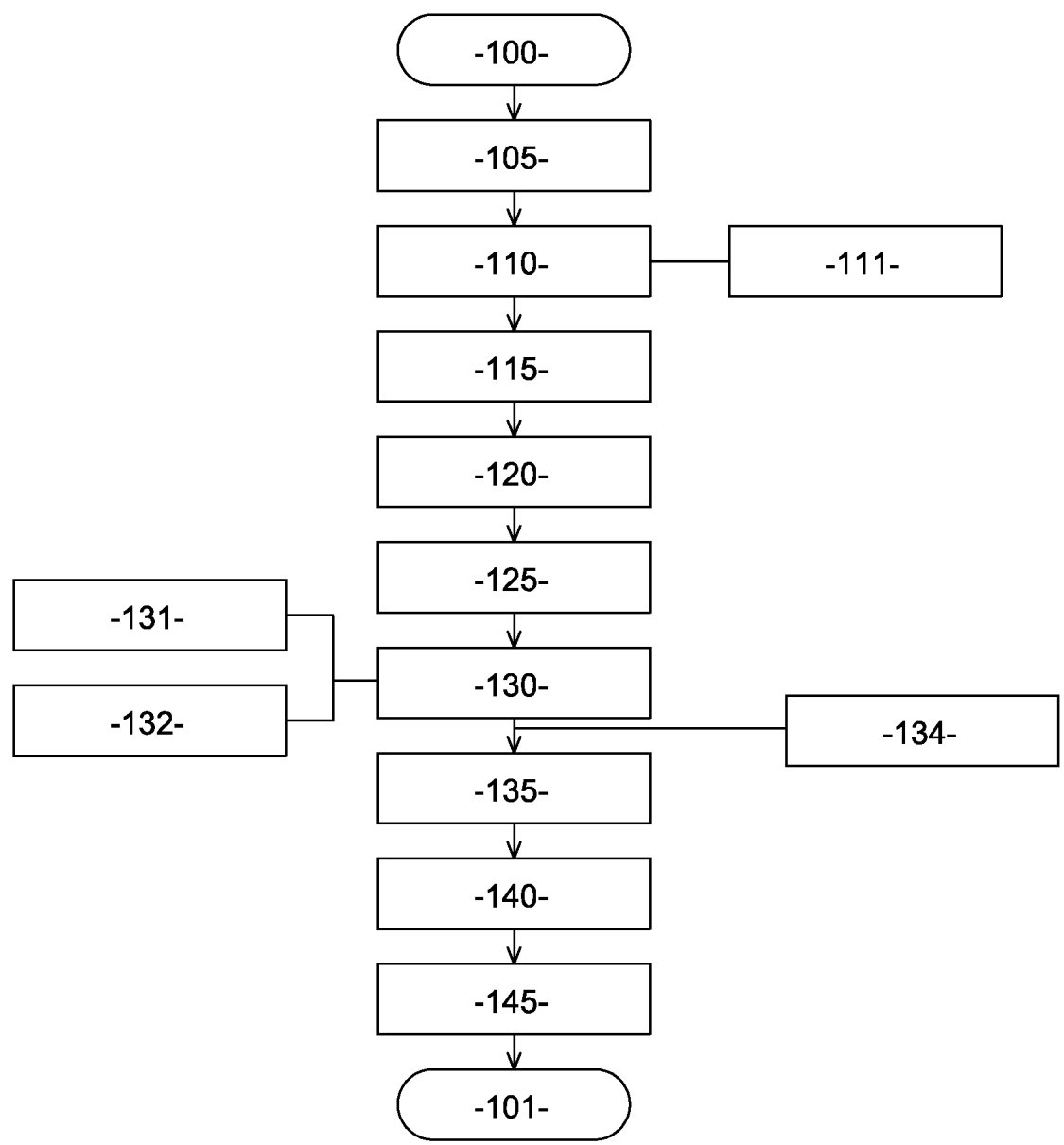

In reference to the figures, a method 100 for assisting in the production of an implantable unfurlable made-to-measure device that can be implanted in a cavity of a body of a living being according to the invention is described below.

The method 100 for assisting in the production of an implantable unfurlable made-to-measure device that can be implanted in a cavity of a body of a living being according to the invention comprises a first step 105 during which three-dimensional reconstruction of a target artery segment 1 is carried out. This reconstruction 105 is carried out based on a series of preoperative radiographic images of the target artery segment 1 of the patient to be operated on. In this instance, the target artery segment 1, also referred to as an arterial lumen, forms a cavity of the body of a living being that is the patient, as defined by the invention. In the example of the target artery segment 1 shown in FIG. 1a, the latter has a main section 5, formed by the thoracic aorta and then the abdominal aorta, that ends at a distal end with a fork forming the aortic bifurcation. At the main section 5, the target artery segment 1 comprises a certain number of collateral arteries 2, of which the right 3 and left 4 iliac arteries and two additional arteries are only shown here in FIG. 1a, such as the common iliac arteries, the internal iliac arteries, the external iliac arteries, the renal arteries, the superior mesenteric artery, the coeliac trunk, the sub-clavian arteries, and the left primitive carotid. The aim of step 105 of the method 100 for assisting in the production of an implantable unfurlable made-to-measure device that can be implanted in a cavity of a body of a living being according to the invention is to produce a three-dimensional reconstruction of a complex surface 6 delimiting the whole of the target artery segment 1 to be instrumented with a made-to-measure endoprosthesis. The techniques of three-dimensional reconstruction based on a series of radiographic images are known per se and will not be described in greater detail here. This allows a digital model of the geometry of the target artery segment 1 to be obtained. For example, in this instance, the three-dimensional reconstruction of the complex surface 6 is produced using a segmentation technique that is known per se, applied to the series of radiographic images, so as to obtain a set of simple surfaces forming the complex surface 6. Furthermore, during the image processing allowing the three-dimensional reconstruction of the target artery segment 1, geometric reference marks are generated along the collateral arteries 2, in particular points constituting a central line specific to each artery and points constituting contours of the arterial lumen around each point constituting the central line specific to each artery, as shown in FIG. 1a.

In a subsequent step 110, the method 100 for assisting in the production of an implantable unfurlable made-to-measure device that can be implanted in a cavity of a body of a living being according to the invention involves producing a first finite element mesh of a geometry of the complex surface 6 determined and reconstructed during step 105. This first mesh is obtained, for example, from the set of simple surfaces forming the complex surface 6, using a mesh algorithm known per se in the finite elements field. The first finite element mesh is then defined by a set of shell elements, each assigned a thickness that can vary depending on the location of the element, an anisotropic elastic behavior law being capable of varying depending on the local composition of the arterial tissue that it represents, a material orientation varying along the arteries and defined at the end of the deformation of the mesh by the morphing. Also, in a sub-step 111, the method 100 for assisting in the production of an implantable unfurlable made-to-measure device that can be implanted in a cavity of a body of a living being according to the invention involves determining a set of geometric parameters of the points of interest 2 formed, in this instance, by the collateral arteries 2, and in particular the ostia of same. These geometric parameters are at least the size and the position of the points of interest 2, in addition to the orientation of the collateral arteries 2 at the ostia of same.

During a step 115, the method 100 for assisting in the production of an implantable unfurlable made-to-measure device that can be implanted in a cavity of a body of a living being according to the invention involves allowing one or more generic components 230, 240, 250 of an unfurlable device 200 that is to be personalized to be chosen in order to tailor it to the patient to be operated on. The generic components 230, 240, 250 are formed from a fabric in the form of simple surfaces such as rotationally symmetrical tubular surfaces and stents in the form of simple three-dimensional curves, and are optionally assembled together to form, in this instance, an endoprosthesis to be personalized. The generic components 230, 240, 250 can originate from a library of digitized generic stents from one or more endoprosthesis manufacturers. In particular, the library can contain bifurcated main bodies, iliac legs, proximal extensions, and covered stents, used in the context of endovascular surgery of aneurysms of the iliac arteries, the abdominal aorta or the thoracic aorta. Since these endoprostheses are generic, they do not have, at this stage, personalized elements such as fenestra, branches, etc.

Next, during a step 120, the method 100 for assisting in the production of an implantable unfurlable made-to-measure device that can be implanted in a cavity of a body of a living being according to the invention involves producing a second finite element mesh of the generic component or components 230, 240, 250 chosen and optionally assembled during step 115. Once again, as with the first mesh, the second mesh is obtained, for example, by a mesh algorithm from a set of simple surfaces or curves originating from the chosen and optionally assembled generic component or components 230, 240, 250. The second finite element mesh is then defined by a set of shell elements for the fabric and beam elements for the stents, assigned a thickness for the fabric and a diameter for the stents depending on the chosen generic components, an orthotropic elastic behavior law for the fabric and an isotropic elastic behavior law for the stents.

It should be noted that steps 105 to 120 can be carried out in any order, provided that step 110 takes place after 105 and that, similarly, step 120 take place after 115.

Once the first and second finite element meshes have been produced, the method 100 for assisting in the production of an implantable unfurlable made-to-measure device that can be implanted in a cavity of a body of a living being according to the invention involves carrying out a step 125, during which step 125 the method 100 according to the invention involves determining parameters of a morphing of the first mesh of the complex surface 6 of the reconstructed target artery segment 1 to the second mesh of the chosen and optionally assembled generic component or components 230, 240, 250. The morphing parameters comprise smooth trajectories of each of the nodes of the first mesh in order to shift from the initial shape shown in FIG. 1*a* to the final shape shown in FIG. 1*b*, the trajectories being determined by the method 100 for assisting in the production of an implantable unfurlable made-to-measure device that can be implanted in a cavity of a body of a living being according to the invention. Once the morphing parameters have been determined, it is possible, by simulation, from the morphing parameters, to deform the first mesh of the complex surface 6 of the target artery segment 1 to a mesh of a geometry of a surface of a set of simple volumes 20, 30, 40, 50 linked to each other representative of the deformed target artery segment 10. This set of simple volumes 20, 30, 40, 50 thus has dimensions that are then adjusted to those of the generic component or components 230, 240, 250 that have been chosen and optionally assembled in order to form the endoprosthesis to be personalized.

Next, in a subsequent step 130, the method 100 for assisting in the production of an implantable unfurlable made-to-measure device that can be implanted in a cavity of a body of a living being according to the invention involves simulating, by the finite elements method, a deformation of the second mesh, by inverse morphing dependent on the previously determined morphing parameters, to the geometry of the complex surface 6, so as to simulate the unfurling of the unfurlable made-to-measure device 200 that is, in this instance, the endoprosthesis to be personalized. This step 130 helps determine how the made-to-measure endoprosthesis that is being prepared will unfurl inside the target artery segment 1 of the patient to be operated on. In particular, during this inverse morphing, the method 100 for assisting in the production of an implantable unfurlable made-to-measure device that can be implanted in a cavity of a body of a living being according to the invention involves imposing, on the nodes of the second mesh, the trajectories, in the opposite direction, determined previously during the morphing of the preceding step 125, until the second mesh is unfurled.

This simulation can be carried out with the second mesh previously inserted, in a sub-step 132, into the first mesh of the complex surface 6 of the cavity 1 that forms, in this instance, the target artery segment.

Thus, once step 130 has been performed, the second mesh of the endoprosthesis to be personalized is unfurled by the inverse morphing that has just been carried out. In particular, during this inverse morphing, the method 100 for assisting in the production of an implantable unfurlable made-to-measure device that can be implanted in a cavity of a body of a living being according to the invention imposes, on the nodes of the second mesh, the trajectories, in the opposite direction, determined previously during the morphing of the preceding step 125, until the second mesh is unfurled inside the first mesh of the complex surface 6, using a solver using the finite element method. The second mesh is then in contact with the first mesh of the complex surface 6. Next, in a step 134, the method 100 for assisting in the production of an implantable unfurlable made-to-measure device that can be implanted in a cavity of a body of a living being according to the invention involves calculating, once again using the finite element method, deformations and constraints induced by the interactions between the first and second meshes.

Optionally, in a step 131 prior to step 130, the method 100 for assisting in the production of an implantable unfurlable made-to-measure device that can be implanted in a cavity of a body of a living being according to the invention involves subjecting the second mesh, by the finite element method, to a deformation simulating a compression of the endoprosthesis 200 to be prepared inside a delivery sheath. This makes it possible to approximate, in an optimal manner, the conditions for implanting the final unfurlable made-to-measure endoprosthesis 200 in the patient to be operated on. It also makes it possible to simulate the insertion of this compressed second mesh into the first mesh into a position close to an optimal position in order to perfect the subsequent real implantation on the patient to be operated on. Moreover, in this way, it is possible to simulate several unfurling positions of the endoprosthesis 200 close to the optimal or initial target position in order to evaluate the impact of inaccurately positioning the endoprosthesis 200 during the subsequent real operation on the patient.

Next, the method 100 for assisting in the production of an implantable unfurlable made-to-measure device that can be implanted in a cavity of a body of a living being according to the invention involves carrying out a step 135 during which a dimensioning is determined of points of interest 2 of the target artery segment 1 present on the first mesh of the complex surface 6 and that are located facing the unfurled second mesh of the endoprosthesis to be produced. In particular, in the case of the endoprosthesis 200 to be personalized, the points of interest are the ostia of the collateral arteries 2. This results, on the endoprosthesis 200 to be personalized, in the marking and creation of fenestra 210 in a wall of the endoprosthesis 200, which fenestra 210 are situated, following the unfurling in the target artery segment 1, facing the abovementioned ostia. In practice, as shown, for example, in FIG. 4, this consists in determining coordinates of the fenestra 210 relative to reference points 251, 260 and to a reference plane defined, for example, by the plane passing through a longitudinal axis A of the generic endoprosthesis 200 to be personalized and a generatrix 252 of same. For example, the reference points can be:

the edge 251 of the top end of the endoprosthesis 200 associated with a first latitude 262; and/or a reference 260 specific to the manufacturer of the generic endoprosthesis 200 to be personalized associated with a second latitude 263.

Associated with the reference plane, a longitude 261 is defined either by a circumferential distance or by an angle. As a variant, the reference plane can be defined relative to the patient who will receive the made-to-measure endoprosthesis 200 that is being prepared.

In order to determine the coordinates and size of the points of interest 2, the method 100 for assisting in the production of an implantable unfurlable made-to-measure device that can be implanted in a cavity of a body of a living being according to the invention involves projecting them from the first mesh of the complex surface 6 onto the second mesh deformed during the unfurling carried out in step 130. The projection is carried out along the axis of the collateral arteries 2 on the second mesh deformed by the inverse morphing of step 130. In particular, this projection consists in determining nodes of the second mesh that are located facing the points of interest 2.

Upon completion of step 135, the method 100 for assisting in the production of an implantable unfurlable made-to-measure device that can be implanted in a cavity of a body of a living being according to the invention involves generating, in a step 140, one or more dimensioned drawings of the unfurlable made-to-measure endoprosthesis 200, in particular of the generic component or components forming the endoprosthesis 200, onto which the dimensioning, i.e. the size and position of the points of interest 2 previously determined in step 135, has been transposed. In particular, the transposing of the dimensioning is carried out based on the coordinates of the nodes of the second mesh previously determined in the non-deformed second mesh. These dimensioned drawings can then be used to actually produce 101 the unfurlable made-to-measure endoprosthesis 200 adapted to the patient who needs to receive it.

In an additional step 145, the method 100 for assisting in the production of an implantable unfurlable made-to-measure device that can be implanted in a cavity of a body of a living being according to the invention involves extracting a set of indicators enabling a practitioner to determine the suitability of the surgical plan to be applied to the patient to be operated on for whom the unfurlable made-to-measure endoprosthesis 200 has been personalized during the preceding steps. This allows him or her to study the influence of the operation parameters, such as the release position of the endoprosthesis 200 inside the target artery segment 1, in order to study the potential impact of inaccuracies in the deployment of the endoprosthesis 200 during the subsequent real operation.

The method 100 for assisting in the production of an implantable unfurlable made-to-measure device that can be implanted in a cavity of a body of a living being according to the invention has been described in reference to an application to made-to-measure vascular endoprostheses intended to be implanted in an arterial lumen. However, the method 100 for assisting in the production of an implantable unfurlable made-to-measure device that can be implanted in a cavity of a body of a living being according to the invention can be implemented for any kind of implantable made-to-measure device, that may or may not be unfurlable, that can be implanted in any cavity of the body of a living being.

Furthermore, the method 100 for assisting in the production of an implantable unfurlable made-to-measure device that can be implanted in a cavity of a body of a living being according to the invention is implemented by a program for controlling a calculator, such as a computer. For this purpose, the control program is saved and stored on a computer support compatible with the calculator. Phases of displaying a result of the different steps of the method 100 for assisting in the production of an implantable unfurlable made-to-measure device that can be implanted in a cavity of a body of a living being according to the invention may be provided, either at the end of a step or during a step.

Naturally, multiple modifications can be made to the invention without departing from the scope of same.

The invention claimed is:

1. A method for assisting in the production of an implantable unfurlable made-to-measure device that can be implanted in a cavity of a body of a living being, based on a series of radiographic images of the cavity, the method comprising steps of:
    a. Three-dimensional reconstruction of a complex surface delimiting a part of the cavity in which the unfurlable made-to-measure device is intended to be installed;
    b. Production of a first finite element mesh of a geometry of the complex surface thus reconstructed;
    c. Choosing of one or more generic components of the unfurlable made-to-measure device that is to be personalized;
    d. Production of a second finite element mesh of the generic component or components chosen and assembled to form the unfurlable made-to-measure device;
    e. Determination of the parameters of a morphing of the obtained first mesh to a mesh of a geometry formed from a set of simple volumes linked to each other representative of the part of the cavity, and then deformation of the first mesh by this morphing;
    f. Simulation, by the finite elements method, of the deformation of the second mesh thus obtained, by inverse morphing, dependent on the previously determined morphing parameters, to the geometry of the complex surface of the cavity, so as to simulate the unfurling of the unfurlable made-to-measure device once installed in the cavity;
    g. Determination of a dimensioning of points of interest of the part in question of the cavity by projecting them onto the second mesh thus deformed; and
    h. Generation of a dimensioned drawing of the generic component or components onto which the previously determined dimensioning has been transposed, the dimensioned drawing allowing the unfurlable made-to-measure device to be produced.

2. The method as claimed in claim 1, characterized in that, during step b, the method comprises a sub-step of determining geometric parameters of points of interest of the part in question of the cavity, the geometric parameters being used during step g.

3. The method as claimed in claim 1, characterized in that, following step e and prior to step f, the second mesh undergoes a deformation simulating a compression of the assembled unfurlable made-to-measure device inside a delivery sheath.

4. The method as claimed in claim 3, characterized in that, following the deformation simulating a compression, the deformed second mesh undergoes a simulation of insertion into the first mesh into a position close to an optimal position.

5. The method as claimed in claim 1, characterized in that, during step f, the method comprises a preliminary step of inserting the second mesh into the deformed first mesh.

6. The method as claimed in claim 5, characterized in that, following step f and prior to step g, the method comprises a step of calculating, by simulation by the finite elements method, deformations and constraints induced by interactions between the first and second meshes following the deformation by inverse morphing of the second mesh to the first mesh.

7. The method as claimed in claim 1, characterized in that, during step g, the projection consists in determining the nodes of the second mesh facing the points of interest.

8. The method as claimed in claim 7, characterized in that, during step h, the transposing of the dimensioning is carried out in the second mesh while the second mesh is not deformed based on the coordinates of the nodes previously determined during step g.

9. The method as claimed in claim 1, characterized in that it comprises an additional step of
   i. Extracting a set of indicators enabling a practitioner to determine the suitability of a preoperative plan.

10. The method as claimed in claim 1, characterized in that, the cavity being an arterial lumen, the unfurlable made-to-measure device is an aortic endoprosthesis.

11. A non-transitory computer medium comprising the recording of a program for controlling a calculator, for implementing the method according to claim 1.

\* \* \* \* \*